United States Patent [19]

Wheeler

[11] Patent Number: 4,524,063
[45] Date of Patent: Jun. 18, 1985

[54] OPHTHALMIC COMPOSITIONS

[75] Inventor: Larry A. Wheeler, Cucamonga, Calif.

[73] Assignee: Allergan Pharmaceuticals, Inc., Irvine, Calif.

[21] Appl. No.: 564,156

[22] Filed: Dec. 22, 1983

[51] Int. Cl.³ .................... A61K 31/74; A61K 31/275
[52] U.S. Cl. ...................................... 424;78; 514/522; 514/912
[58] Field of Search ............... 424/304, 286, 78

[56] References Cited

U.S. PATENT DOCUMENTS 3,962,308  6/1976  Sinkula ...................... 260/465 D
4,067,995  1/1978  Wright et al. .................... 424/304

OTHER PUBLICATIONS

Chem. Abst., 61 539(f), (1964)—Krishna et al.
Chem. Abst., 81 120281m, (1974)—Hall et al.
Symposium on Ocular Therapy, 9, 1-16, (1977)—Maichuk.
Chem. Abst., 89 16840x, (1978)—Johnson et al.
Chem. Abst., 92 87854c, (1980)—Johnson et al.
Chem. Abst., 98 154907m, (1983)—Cheney et al.

Primary Examiner—Douglas W. Robinson
Attorney, Agent, or Firm—Joseph A. Marlino; Stuart R. Suter; Alan D. Lourie

[57] ABSTRACT

A topical lodoxamide composition having enhanced efficacy for treatment of ocular allergic diseases. The composition comprises the addition of polyvinyl alcohol to an aqueous solution containing lodoxamide tromethamine.

4 Claims, No Drawings

OPHTHALMIC COMPOSITIONS

This invention relates to topical compositions for the treatment of ocular allergic diseases. More particularly, this invention relates to topical compositions containing lodoxamide tromethamine, di-[tris(hydroxymethyl)methylammonium]-N-N'-(2-chloro-5-cyano-m-phenylene)dioxamate having the following structure.

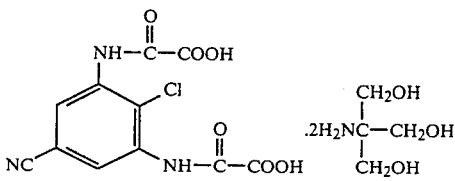

This compound is disclosed, for example, in U.S. Pat. No. 3,962,308 and the USAN (USP dictionary of drug names).

Lodoxamide is cromolyn-like in activity and is employed for the prophylatic treatment of mast cell mediated allergic diseases. The compound is orally active. It has also been reported to have been formulated with pharmaceutical carriers for parenteral, inhalation and rectal means of administration for anti-asthmatic anti-allergic and anaphylatic reactions.

However, compounds having this cromolyn-like activity such as, for example, lodoxamide and disodium cromoglycate are not topically effective as ocular anti-allergic agents. There has been a long standing problem in attempting to formulate a topical preparation which would inhibit mast cell mediators in the eye, i.e., produce anti-allergic activity.

It is therefore an object of this invention to provide an ophthalmic vehicle which would enhance the immediate efficacy of lodoxamide tromethamine for the topical treatment of ocular allergic diseases.

The problem has now been solved by the novel pharmaceutical ophthalmic vehicle of the present invention. It has been unexpectedly discovered that when polyvinyl alcohol is added to an aqueous solution containing lodoxamide it results in a composition that significantly enhances the topical efficacy of lodoxamide for the treatment of ocular allergic reactions.

The basic activity of the compounds of this invention is demonstrated by employing a modified standard pharmacological test for inhibiting the passive ocular anaphylaxis in rat conjunctiva as reported by Iso (*Ophthalmic Res.* 12:9–15, 1980). Briefly, this procedure comprises injecting an antibody around the eye which binds to mast cells. An antigen solution also containing a blue dye is given I.V. When the antigen combines with the antibody bound to the mast cells, it releases inflammatory substances. Since inflammatory signs such as red eye or other irritation are not noticeable in the rat, these allergic reactions are determined by estimating the leakage of dye in the tissue as a parameter of the increased vascular permeability during anaphylaxis.

Lodoxamide tromethamine was examined in several pharmaceutical ophthalmic formulations for the topical efficacy and potency in inhibiting the release of mast cell mediators in the eye in the above modified Iso test. Ten ul drops of each formula were applied to the eyes 15 minutes prior to, just before, and 15 minutes after the antigen challenge.

The results of this test are set forth in Table 1.

TABLE 1

| % Lodoxamide | % Inhibition in an Aqueous Solution | % Inhibition in an Aqueous Solution + 3% PVA* |
| --- | --- | --- |
| 0.1 | 0 | 0 |
| 0.5 |   | 18 |
| 1.0 | 0 | 33 |
| 3.0 |   | 43 |
| 5.0 | 0 | 63 |
| 10.0 |   | 64 |

*Polyvinyl Alcohol

The above results of Table 1 demonstrate that topical applications of lodoxamide in concentrations of 0.1, 1, and 5% in an aqueous solution did not have any inhibitory effect on dye leakage, i.e., anti-allergic activity. When polyvinyl alcohol is added to the solution, significant topical efficacy is noted. For example, the percent inhibition of the dye leakage response increased dramatically from 0% to 63% when the substantivity of the formula was increased with polyvinyl alcohol. The results indeed indicate the significant topical efficacy has been achieved in the above rat passive ocular anaphylaxis assay with the addition of PVA to the formula.

In contrast to the above results obtained by topical administration of lodoxamide tromethamine, intravenous administration of concentrations of 0.2, 1 and 3 mg./kg. resulted in 80%, 95%, and 96% inhibition, respectively, in the ocular assay.

Disodium cromoglycate, which is the prototypical mast cell stabilizer, was also tested in the above modified Iso procedure. Like lodoxamide, the compound was not found to be topically effective when administered in an aqueous solution. However, unlike lodoxamide the addition of polyvinyl alcohol to the aqueous solution containing disodium cromoglycate did not in any way enhance the topical efficacy. Both compounds were found efficacious in inhibiting ocular anaphylaxis in the rat after intravenous administration.

In summary, although intravenous administration of lodoxamide is efficacious in inhibiting ocular anaphylaxis in the rat, topical application of up to 5% concentration in an aqueous solution is not effective. The addition of polyvinyl alcohol to the aqueous solution markedly enhanced the topical efficacy of the lodoxamide.

The polyvinyl alcohol may be present in the aqueous solution in an amount of from 1% to about 5%. Most advantageously, the polyvinyl alcohol is present in an amount of about 3%.

The lodoxamide tromethamine may be present in the composition of this invention in an amount of from 1.0% to 10.0%. Most advantageously in an amount about 5%.

The ophthalmic solutions are sterile and can contain in addition to the compounds listed above antimicrobial agents. Exemplary of such agents are the quaternary ammonium germicides such as benzalkonium chloride, benzethonium chloride or cetylpyridium chloride. Other such agents that can be employed are chlorobutanol or phenylmercuric nitrate. If antioxidants are required, sodium sulfite, sodium ascorbate or other ophthalmologically acceptable antioxidants known to the art such as oxime sulfate may be used.

EXAMPLE

| Ingredients | Amounts W/V |
| --- | --- |
| Lodoxamide Tromethamine | 5.0 gms. |

-continued

| Ingredients | Amounts W/V |
| --- | --- |
| Polyvinyl Alcohol | 3.0 gms. |
| Distilled Water q.s. | 100.0 ml. |

The polyvinyl alcohol and distilled water are mixed with stirring while heating. The lodoxamide is then added to this solution with stirring.

The composition is applied topically to the eye.

We claim:

1. A pharmaceutical composition for the treatment of ocular allergic diseases containing a pharmaceutically acceptable ophthalmic vehicle comprising from about 1.0% to about 5.0% polyvinyl alcohol and from about 1.0% to about 10.0% lodoxamide tromethamine in an aqueous solution.

2. The composition of claim 1 in which the polyvinyl alcohol is present in a 3% concentration and lodoxamide is present in a 5.0% concentration.

3. The composition of claim 1 in which the alcohol is present in a 3% concentration.

4. The composition of claim 1 in which the lodoxamide is present in a 5% concentration.

* * * * *